(12) United States Patent
Zhang et al.

(10) Patent No.: US 10,639,295 B2
(45) Date of Patent: May 5, 2020

(54) PODOPHYLLOTOXIN DERIVATIVE WITH 4-POSITION NITROGEN SUBSTITUTION AND PREPARATION METHOD AND APPLICATION THEREOF

(71) Applicant: YAOPHARMA CO., LTD., Chongqing (CN)

(72) Inventors: Zhirong Zhang, Sichuan (CN); Meiling Zhou, Sichuan (CN); Yan Zhang, Chongqing (CN)

(73) Assignee: YAOPHARMA CO., LTD., Chongqing (CN)

( * ) Notice: Subject to any disclaimer, the term of this patent is extended or adjusted under 35 U.S.C. 154(b) by 0 days.

(21) Appl. No.: 16/085,577

(22) PCT Filed: Aug. 2, 2016

(86) PCT No.: PCT/CN2016/092829
§ 371 (c)(1),
(2) Date: Sep. 16, 2018

(87) PCT Pub. No.: WO2017/156959
PCT Pub. Date: Sep. 21, 2017

(65) Prior Publication Data
US 2019/0029997 A1  Jan. 31, 2019

(30) Foreign Application Priority Data
Mar. 17, 2016  (CN) .......................... 2016 1 0151988

(51) Int. Cl.
*A61K 31/365* (2006.01)
*A61K 31/496* (2006.01)
(Continued)

(52) U.S. Cl.
CPC .......... *A61K 31/365* (2013.01); *A61K 9/0019* (2013.01); *A61K 31/496* (2013.01);
(Continued)

(58) Field of Classification Search
CPC .................................................... C07D 493/04
See application file for complete search history.

(56) References Cited

U.S. PATENT DOCUMENTS

| 5,332,811 A | 7/1994 | Lee et al. |
| 2016/0289242 A1 | 10/2016 | Tang et al. |

FOREIGN PATENT DOCUMENTS

| CN | 101074233 A | 11/2007 |
| CN | 102875564 A | 1/2013 |

(Continued)

OTHER PUBLICATIONS

Goodman & Gilman's The Pharmacological Basis of Therapeutics, Tenth Ed. 2001, Chapter 1; pp. 1-29.*
Kerns, Edward et al, Drug-like Properties: Concepts, Structure Design and Methods: from ADME to Toxicity Optimization, (Elsevier, 2008) pp. 92-93.*
(Continued)

*Primary Examiner* — Valerie Rodriguez-Garcia
(74) *Attorney, Agent, or Firm* — Yue (Robert) Xu; Apex Attorneys at Law, LLP

(57) ABSTRACT

A compound represented by formula (I) or a pharmaceutically acceptable salt thereof, and a pharmaceutically acceptable formulation prepared using the compound and the salt. The compound represented by formula (I) or the pharmaceutically acceptable salt exhibits significantly higher buildup and concentration in the lungs compared to other
(Continued)

tissues, a longer dwell time in the lungs, and/or elevated pharmaceutical efficacy.

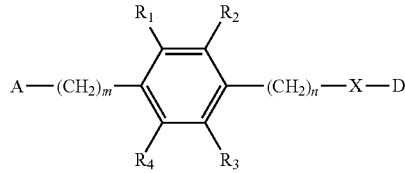

Formula (I)

6 Claims, 2 Drawing Sheets

(51) Int. Cl.
C07D 493/04 (2006.01)
A61K 47/54 (2017.01)
A61P 37/06 (2006.01)
A61P 11/00 (2006.01)
A61P 35/00 (2006.01)
A61K 9/00 (2006.01)
A61K 31/135 (2006.01)
A61K 31/573 (2006.01)

(52) U.S. Cl.
CPC .......... A61K 47/545 (2017.08); A61K 47/555 (2017.08); A61P 11/00 (2018.01); A61P 35/00 (2018.01); A61P 37/06 (2018.01); C07D 493/04 (2013.01); A61K 31/135 (2013.01); A61K 31/573 (2013.01)

(56) References Cited

FOREIGN PATENT DOCUMENTS

| CN | 103304574 A | 9/2013 |
| CN | 103601732 A | 2/2014 |
| CN | 103613600 A | 3/2014 |
| CN | 103690512 A | 4/2014 |
| CN | 104523597 A | 4/2015 |
| CN | 105037379 A | 11/2015 |
| CN | 105732651 A | 7/2016 |
| JP | 63-23884 | * 2/1988 |
| JP | S6323884 A | 2/1988 |
| WO | 9009788 A1 | 9/1990 |

OTHER PUBLICATIONS

Swarbrick et al. (Encyclopedia of Pharmaceutical Technology 13 (Marcel Dekker, NY 1996) pp. 453-499).*
Stahl et al. (eds., Handbook of pharmaceutical salts. Properties, selection and use (Wiley-VCH, 2008), pp. 265-327).*
On-line Medical Dictionary (Jul. 7, 2005).*
Raw machine translation of description for JP 63-23884 (Feb. 1988).*
International Search Report for PCT/CN2016/092829 dated Dec. 15, 2016, ISA/CN.
Sung Jin Cho,Antitumor Agents. 163. Three-Dimensional Quantitative Structure-Activity Relationship Study of 4'-O-Demethylepipodophyllotoxin Analogs Using the Modified CoMFA/q2-GRS Approach, Journal of Medicinal Chemistry, 1996, vol. 39, No. 7,pp. 1383-1395.
Maria Duca, Triple Helix-Forming Oligonucleotides Conjugated to New Inhibitors of Topoisomerase II: Synthesis and Binding Properties,Bioconjugate Chem. 2005, 16, 873-884.
Ahmed Kamal,4β-[4'-(1-(Aryl)ureido)benzamide]podophyllotoxins as DNA topoisomerase I and IIa inhibitors and apoptosis inducing agents,Bioorganic & Medicinal Chemistry, Bioorganic & Medicinal Chemistry 21 (2013) 5198-5208.
Zhang Zhihua, Advances in studies on podophyllotoxin C-4β-N-linked derivatives, Chinese Traditional Patent Medicine,Dec. 31, 2015, vol. 37, No. 12,pp. 2733-2738.
The European Search Report dated Oct. 7 2019 for Australian European No. 16894120.1.
Naik P K et al: "The binding modes and binding affinities of epipodophyllotoxin derivatives with human topoisomerase II@a",Journal of Molecular Graphics and Modelling, Elsevier Science, New York, NY, US, vol. 29, No. 4, Dec. 1, 2010 (Dec. 1, 2010), pp. 546-564.
Xiao Z et al: "Antitumor agents. 213. Modeling of epipodophyllotoxin derivatives using variable selection k nearest neighbor QSAR method", Journal of Medicinal Chemistry, American Chemical Society, US, vol. 45, No. 11, May 23, 2002 (May 23, 2002), pp. 2294-2309.

* cited by examiner

PODOPHYLLOTOXIN DERIVATIVE WITH 4-POSITION NITROGEN SUBSTITUTION AND PREPARATION METHOD AND APPLICATION THEREOF

CROSS REFERENCE TO RELATED APPLICATIONS

This application is a US National Phase application based upon PCT Application No. PCT/CN2016/092829, filed on Aug. 02, 2016, which claims the priority of Chinese Patent Application No. 201610151988.0, filed on Mar. 17, 2016, and the disclosures of which are hereby incorporated by reference.

FIELD

The present disclosure relates to the field of medicine, specifically to a small molecular lung-targeting drug, and its use for preparing drugs that prevent and control pneumonia, bronchitis, lung tumor, rejections after lung transplantation and other lung diseases.

BACKGROUND

Lung is an important respiratory organ of the human body and is the main place for gas exchange. Normal lung function is the guarantee for life. Therefore, lung disease is one of the common diseases that threaten human life and health, including pneumonia, bronchitis, lung cancer, pulmonary tuberculosis, emphysema and so on. Since most lung diseases require long-term drug treatment, it is especially important to increase the safety and effectiveness of the drugs and reduce the toxicity and side effects.

The lung-targeting drug delivery system can specifically concentrate the drug in the lung, increase the concentration of the drug in the lung or increase the retention time of the drug in the lung, thereby improving the efficacy of the drug and reducing the systemic toxicity and side effects. Therefore, the study of lung-targeting drug delivery system is significantly important for the treatment of lung diseases.

At present, the lung-targeting drug delivery system under research is mainly particles drug delivery system, such as microspheres, microcapsules, liposomes, nanoparticles, etc. After the particles are intravenously injected into the body, the drug-containing particles arrive at the lung through blood circulation, they may be engulfed by the reticuloendothelial system of the lung tissue or mechanically ingested by the lung capillaries, so that the drug can be concentrated in the lung tissue. However, there are some problems to be solved in the particles drug delivery system. For example, the problem of drug burst, the particle diameter and the particle size are hard to be strictly controlled, the drug loading is low, the stability is not good, the preparation process is complicated, and it is difficult to be produced in large-scale. In addition, other lung-targeting carriers include peptides, proteins, vitamins, polysaccharides, monoclonal antibodies, etc., but most of these carriers are macromolecular substances, and the drug-carrier conjugate structure after preparation is unclear, the quality is difficult to be put under strictly control, and it is difficult to be developed into new drugs.

Thus, it is necessary to develop a small molecular lung-targeting drug that has clear curative effect, safe and reliable, and the quality of which is easy to be controlled.

SUMMARY

The present disclosure provides a compound represented by Formula I or a pharmaceutically acceptable salt thereof:

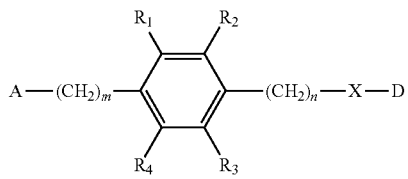

Formula I wherein,
m=0, 1, 2, 3, 4;
n=0, 1, 2, 3, 4;
$R_1$, $R_2$, $R_3$, $R_4$ are each independently selected from the group consisting of hydrogen, halogen, hydroxyl, mercapto, nitro, amino, acetyl amino, cyano, acetoxy, acetate, C1~C4 alkyl, C1~C4 alkoxy, trifluoromethyl and trifluoromethoxy;
A is

and $R_5$ and $R_6$ are each independently selected from the group consisting of hydrogen, C1~C6 alkyl, C3~C7 cycloalkyl, C1~C5 alkylamino C1~C5 alkyl, and di-(C1~C5 alkyl)amino C1~C5 alkyl,
or A is a 5 to 6 membered heterocyclic ring or substituted heterocyclic ring containing 1 to 2 nitrogen atoms, and the substituent of the substituted heterocyclic ring is selected from the group consisting of halogen, hydroxyl group, mercapto group, nitro group, C1~C4 alkyl and C1~C4 alkoxy;
X is optionally selected from the group consisting of

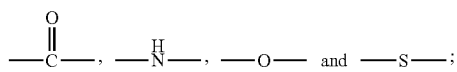

and
D is preferably a known drug or biological active compound with a molecular weight of less than 1000 Dalton used for treating lung diseases, and the D and the X are connected via a covalent bond; specifically, through an acylation reaction or etherification reaction, D and X are linked by forming amide, ether or thioether together.

In the present disclosure, the drug D for treating lung diseases includes but is not limited to: antineoplastic, anti-inflammatory drug, antiviral drug, anti-tuberculosis drug, anti-microbial drug, immunosuppressant and so on.

Antineoplastic: for example podophyllotoxin, etoposide, tripterine, gemcitabine, fluorouracil, chlorambucil, cyclophosphamide, melphalan, paclitaxel and vinblastine, and analog and/or derivative thereof.

Anti-inflammatory drug: for example non-steroidal (indomethacin, ibuprofen and analog and/or derivative thereof), steroids (cortisone, hydrocortisone, dexamethasone, prednisone, and analog and/or derivative thereof).

Antiviral drug: for example zidovudine, zalcitabine, acyclovir, ribavirin, amantadine hydrochloride and vidarabine, and analog and/or derivative thereof.

Anti-tuberculosis drug: for example isoniazid, rifampicin, pyrazinamide, ethambutol, and analog and/or derivative thereof.

Anti-microbial drug: for example penicillins (amoxicillin, ciclacillin and analog and/or derivative), cephalosporins (cephalexin, cefradine and analog and/or derivative), tetracyclines (tetracycline hydrochloride, doxycycline and analog and/or derivative).

Immunosuppressant: for example triptolide, cyclosporin, tacrolimus, rapamycin, mycophenolate mofetil, mizoribine and analog and/or derivative.

In the present disclosure, the pharmaceutically acceptable salt of the compound is a salt formed from the compound and an inorganic acid or an organic acid, wherein the acid comprises hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, niacin, camphoric acid, gluconic acid, glucuronic acid, pamoic acid, methanesulfonic acid, ethanesulfonic acid, sulfamic acid and p-toluenesulfonic acid.

In the present disclosure, the pharmaceutically acceptable preparation formed from the compound or the pharmaceutically acceptable salt thereof includes, but is not limited to tablet, suppository, soft capsule, hard capsule, solution, suspension, aerosol, injection, lyophilized powders for injection, sustained-release controlled-release preparation and various particles drug delivery systems; and the preparation may be administered by mouth, nasal, rectal, transdermal or injection.

The present disclosure also provides a method for preparing drugs that prevent and control pneumonia, bronchitis, lung tumor, rejections after lung transplantation and other lung diseases using the compound or the pharmaceutically acceptable salt thereof of the present disclosure.

On the other hand, the present disclosure also provides a method for preventing or controlling pneumonia, bronchitis, lung tumor, rejections after lung transplantation and other lung diseases, comprising administering the compound or the pharmaceutically acceptable salts thereof of the present disclosure to the subjects suffering from the diseases.

The present disclosure further provides a method for preparing the small molecular lung-targeting compound of the present disclosure:

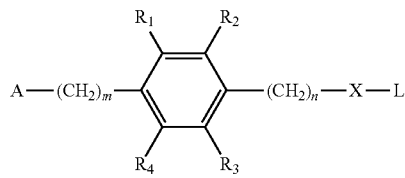

and D are subjected to an acylation reaction or an etherification reaction to give the compound represented by Formula I, wherein:

m=0, 1, 2, 3, 4;

n=0, 1, 2, 3, 4;

L is a leaving group, which includes but is not limited to hydroxy, mercapto group, halogen, amino group, methoxy group, ethoxy, tert-butoxy, azido group and so on;

$R_1$, $R_2$, $R_3$, $R_4$ are each independently selected from the group consisting of hydrogen, halogen, hydroxyl, mercapto, nitro, amino, acetyl amino, cyano, acetoxy, acetate, C1~C4 alkyl, C1~C4 alkoxy, trifluoromethyl and trifluoromethoxy;

A is

and $R_5$ and $R_6$ are each independently selected from the group consisting of hydrogen, C1~C6 alkyl, C3~C7 cycloalkyl, C1~C5 alkylamino C1~C5 alkyl, and di-(C1~C5 alkyl)amino C1~C5 alkyl, or A is a 5 to 6 membered heterocyclic ring or substituted heterocyclic ring containing 1 to 2 nitrogen atoms;

X is optionally selected from the group consisting of

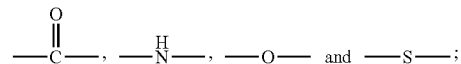

and

D is optionally selected from the group consisting of antineoplastic, anti-inflammatory drug, antiviral drug, anti-tuberculosis drug, anti-microbial drug and immunosuppressant.

The present disclosure further provides a small molecular lung-targeting podophyllotoxin derivative.

Podophyllotoxin is a kind of natural product having obvious antitumor activity, which has strong killing effect on many kinds of tumor cells and a broad-spectrum antitumor activity. However, due to the serious toxicity and side effects of podophyllotoxin, especially its serious damage on stomach and intestine, the use of podophyllotoxin as an antineoplastic is limited. Since the 1950s, many modifications have been made to podophyllotoxin, and researches have synthesized thousands of derivatives, aiming to obtain a derivative that has small toxicity and side effects and strong antitumor activity. Wherein the C-4β-glycosyl substituted derivative etoposide (VP-16) and the teniposide (VM-26) have been successfully used in clinical practice and become the first-line treatment for small cell lung cancer. However, neither etoposide nor teniposide has lung-targeting effect, which not only decreases the curative effect, but also causes different range of toxicity and side effects on other tissues and organs. Studies have shown that the adverse reaction of etoposide mainly manifested in severe bone marrow suppression, which is a dose-limiting toxicity. In addition, there is also severe a gastrointestinal reaction, a certain degree of neurotoxicity, cutaneous anaphylaxis, alopecia and so on. Therefore, it is still an important spot in the study to modify the structure of podophyllotoxin so as to find a highly effective and low toxic antineoplastic drug, which will be important for promoting podophyllotoxin targeting to lung. Researches have shown that podophyllotoxin derivative with 4-position nitrogen substitution can significantly enhance antitumor activity, such as 4β-amino-4'-demethyl-epipodophyllotoxin. Thus, the present disclosure further provides a lung-targeting podophyllotoxin derivative with 4-position nitrogen substitution. More specifically, podophyllotoxin derivative with 4-position nitrogen substitution is

[Structure: A-CH2-C6H4-C(=O)-NH-podophyllotoxin scaffold with OH, OMe groups]

wherein:

A is $$-N \begin{matrix} R_5 \\ R_6 \end{matrix},$$

and $R_5$ and $R_6$ are each independently selected from the group consisting of C1~C3 alkyl, C3~C7 cycloalkyl, C1~C3 alkylamino C1~C3 alkyl, and di-(C1~C3 alkyl)amino C1~C3 alkyl, or A is selected from the group consisting of

[Structures: pyrrolidin-1-yl, piperidin-1-yl, piperazin-1-yl, 4-methylpiperazin-1-yl groups] and The present disclosure further provides a method for preparing the small molecular lung-targeting podophyllotoxin derivative:

reacting

[Structure: A-CH2-C6H4-C(=O)-OH]

with 4β-amino-4'-demethylepipodophyllotoxin to give the small molecular lung-targeting podophyllotoxin derivative, and the reaction equation is shown hereinafter:

[Structure: A-CH2-C6H4-C(=O)-OH] +

[Structure: 4β-amino-4'-demethylepipodophyllotoxin with NH2 group]

→

[Structure: Final product with amide linkage]

wherein:

A is $$-N \begin{matrix} R_5 \\ R_6 \end{matrix},$$

and $R_5$ and $R_6$ are each independently selected from the group consisting of C1~C3 alkyl, C3~C7 cycloalkyl, C1~C3 alkylamino C1~C3 alkyl, and di-(C1~C3 alkyl)amino C1~C3 alkyl, or A is selected from the group consisting of

[Structures: pyrrolidin-1-yl, piperidin-1-yl, piperazin-1-yl, 4-methylpiperazin-1-yl groups] and More specifically, by reacting N,N,N'-trimethyl-N'-(4-carboxybenzyl)-1,3-propanediamine and 4-(4-methylpiperazin-1-ylmethyl)benzoic acid with 4β-amino-4'-demethylepipodophyllotoxin under the reaction of 2-(7-azobenzotriazole)-N,N,N',N'-tetramethyluron hexafluorophosphate (HATU) and the triethylamine, respectively, compounds DC and DP are prepared.

The structural formula of compounds DC and DP are shown hereinafter,

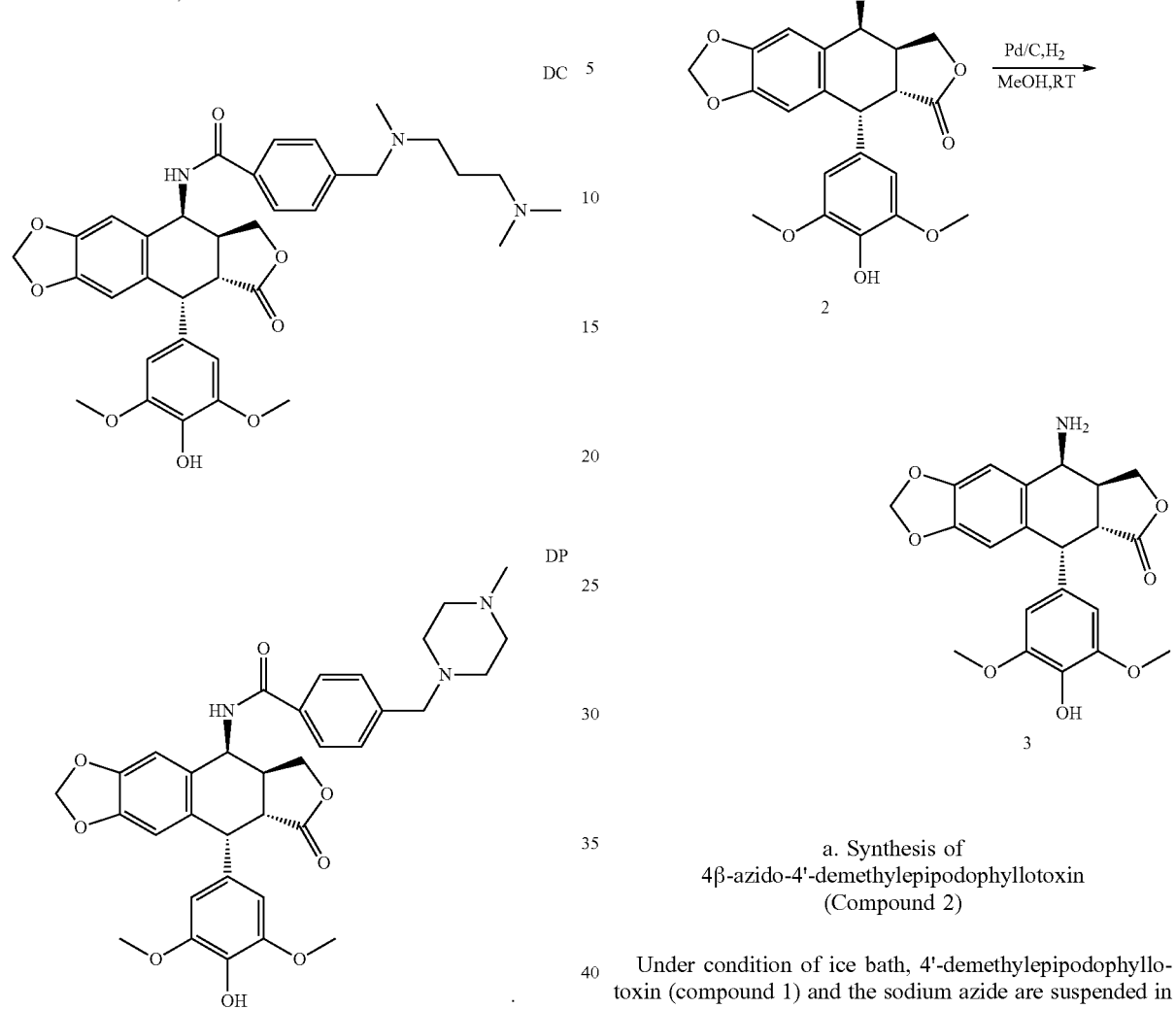

The method for synthesizing compounds DC and DP will be illustrated briefly hereinafter.

(1) 4β-Amino-4'-Demethylepipodophyllotoxin is Synthesized by the Method Provided by J. Med. Chem, 1991(34):3346-3350

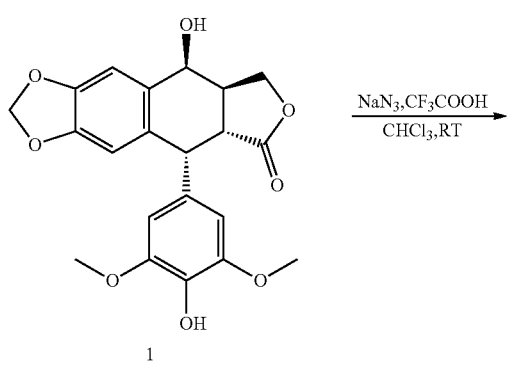

a. Synthesis of 4β-azido-4'-demethylepipodophyllotoxin (Compound 2)

Under condition of ice bath, 4'-demethylepipodophyllotoxin (compound 1) and the sodium azide are suspended in trichloromethane, and trifluoroacetic acid is slowly added dropwise under stirring. The temperature of the mixture is raised to room temperature, and the mixture is stirred overnight. After the completion of the reaction is detected by TLC, saturated sodium carbonate solution is added and the organic layer is separated, which is washed with the saturated saline, and fully dried with anhydrous sodium sulfate. The desiccant is removed by filtration, and the solution is evaporated to dryness under reduced pressure. The crude product is purified by silica gel column chromatography to give a white foam like solid, i.e., compound 2.

b. Synthesis of 4β-amino-4'-demethylepipodophyllotoxin (Compound 3)

Under condition of room temperature, compound 2 and 10% Pd/C are suspended in anhydrous methanol, and reduced by introducing hydrogen. The reaction is carried out overnight at room temperature. After the completion of the reaction is detected by TLC, the catalyst is removed by filtration, and the solution is evaporated to dryness under reduced pressure. The crude product is purified by silica gel column chromatography to give a white solid, i.e., compound 3.

(2) Synthesis of N,N,N'-trimethyl-N'-(4-carboxybenzyl)-1,3-propanediamine

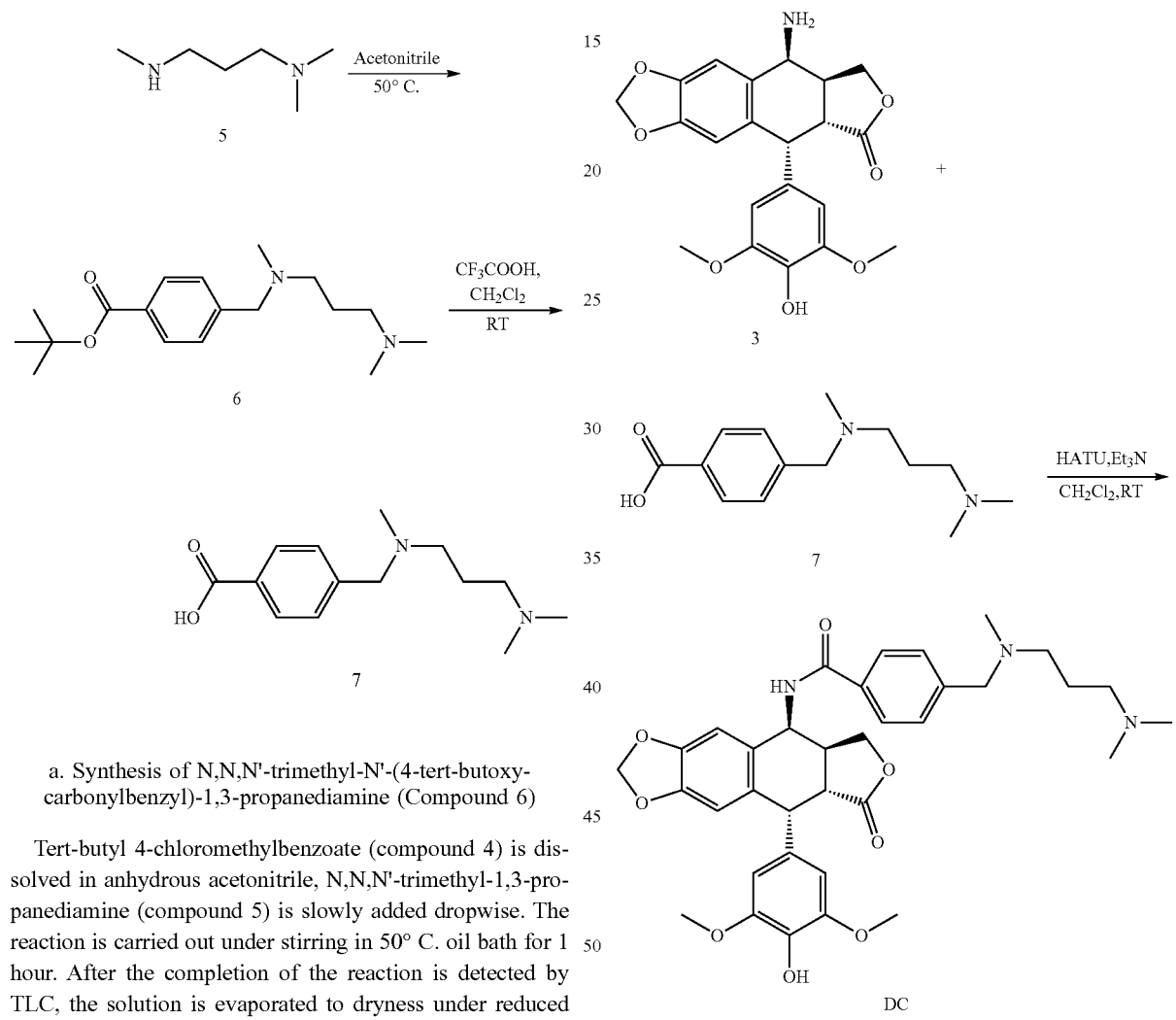

a. Synthesis of N,N,N'-trimethyl-N'-(4-tert-butoxycarbonylbenzyl)-1,3-propanediamine (Compound 6)

Tert-butyl 4-chloromethylbenzoate (compound 4) is dissolved in anhydrous acetonitrile, N,N,N'-trimethyl-1,3-propanediamine (compound 5) is slowly added dropwise. The reaction is carried out under stirring in 50° C. oil bath for 1 hour. After the completion of the reaction is detected by TLC, the solution is evaporated to dryness under reduced pressure. The crude product is purified by silica gel column chromatography to give a faint yellow oil product, i.e., compound 6.

b. Synthesis of the N,N,N'-trimethyl-N'-(4-carboxybenzyl)-1,3-propanediamine (Compound 7)

Under condition of ice bath, the compound 6 is dissolved in dichloromethane, and trifluoroacetic acid is slowly added dropwise under stirring. The reaction is carried out under stirring for 3 hours in ice bath. After the completion of the reaction is detected by TLC, the solution is evaporated to dryness under reduced pressure to give a faint yellow oil product. The crude product is dissolved in a small amount of methanol and hydrogen chloride gas is introduced therein. The product is salted under appropriate stirring, and the solution is evaporated to dryness under reduced pressure, followed by recrystallization in acetone-methanol to give a white solid, i.e., compound 7.

(3) Synthesis of Compound DC

Compound 3 and compound 7 are weighed and put into a round bottom flask, anhydrous dichloromethane is added, and then 2-(7-azobenzotriazole)-N,N,N',N'-tetramethyluronium hexafluorophosphate (HATU) and triethylamine are added. The reaction is carried out under stirring at room temperature for 3 hours. The solution is evaporated to dryness under reduced pressure. The crude product is purified by silica gel column chromatography to give a faint yellow solid, i.e., compound DC.

(4) Synthesis of Compound DP

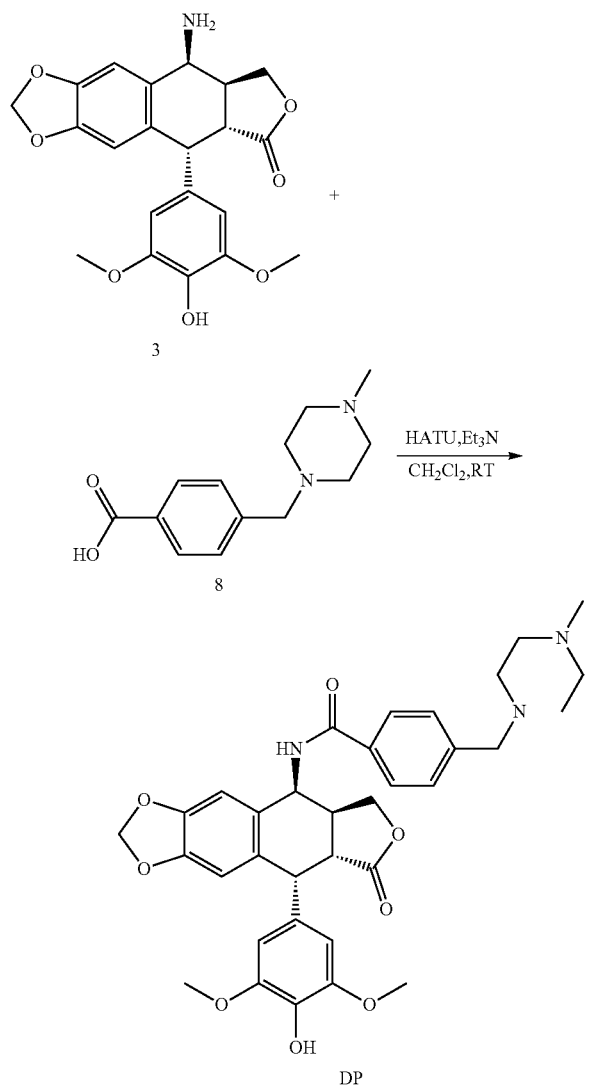

Compound 3 and compound 8 are weighed and put into a round bottom flask, anhydrous dichloromethane is added, and then 2-(7-azobenzotriazole)-N,N,N',N'-tetramethyluronium hexafluorophosphate (HATU) and triethylamine are added. The reaction is carried out under stirring at room temperature for 3 hours. The solution is evaporated to dryness under reduced pressure. The crude product is purified by silica gel column chromatography to give a faint yellow solid, i.e., compound DP.

Wherein compound 8 is a common raw material in the chemical industry, which can be purchased on the market.

Another object of the present disclosure is to provide a use of the small molecular lung-targeting compound or the pharmaceutically acceptable salts thereof of the present disclosure for preparing drugs that prevent and treat lung diseases with.

The lung diseases include pneumonia, bronchitis, lung tumor, rejection after lung transplantation and other lung diseases.

The beneficial effects of the present disclosure are illustrated hereinafter.

In order to demonstrate the lung-targeting ability of the small molecular lung-targeting compound of the present disclosure or the pharmaceutically acceptable salt thereof, the above compounds are subjected to in vivo drug distribution test and in vivo efficacy test. The test results show that the small molecular lung-targeting compound prepared by the present disclosure or the pharmaceutically acceptable salt thereof has significantly higher lung aggregation concentration and lung retention time than other tissues, so that the curative effect is improved and/or the dosage is reduced, and the occurrence of toxicity and side effects is reduced, and the effectiveness and safety of the product is further improved.

The experiments disclosed in the present disclosure are merely exemplary experiments in numerous experiments in the development of the present disclosure, which merely aim at illustrating the lung-targeting ability of the compounds of the present disclosure and their effectiveness and safety.

DETAILED DESCRIPTION

Figure 1:
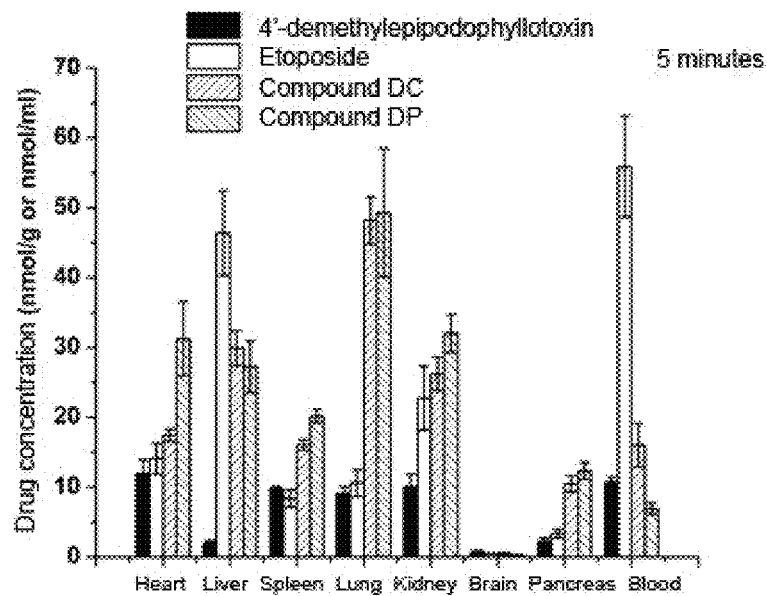
FIG. 1 is a concentration distribution profile of 4'-demethylepipodophyllotoxin, etoposide, compound DC and compound DP in tissues after 5 minutes administration by tail vein injection.

The small molecular lung-targeting compound related to the present disclosure and the method for preparing the same will be further illustrated in combination with examples hereinafter. It is not limited to the present disclosure, and the modifications by one of ordinary skill in the art with the common knowledge are within the scope of the present disclosure.

EXAMPLE 1

Synthesis of 4β-amino-4'-demethylepipodophyllotoxin a. Synthesis of 4β-azido-4'-demethylepipodophyllotoxin (Compound 2)

Under condition of ice bath, 400 mg (1 mmol) of 4'-demethylepipodophyllotoxin (compound 1) and 325 mg (5 mmol) of sodium azide were suspended in trichloromethane (40 mL) in a 100 mL round-bottom flask, and 2 mL of trifluoroacetic acid was slowly dropped under stirring. The temperature of the mixture was raised to room temperature, and the mixture was stirred overnight. After the completion of the reaction was detected by TLC, 25 mL of saturated sodium carbonate solution was added and the organic layer was separated, which was washed with saturated saline (25 mL×2) and fully dried with anhydrous sodium sulfate. The desiccant was removed by filtration, and the solution was evaporated to dryness under reduced pressure. The crude product was purified by silica gel column chromatography (ethyl acetate:petroleum ether=5:2) to give 390 mg of pure compound 2, which was a white foam like solid. The yield was 91.8%.

$^1$H-NMR (400 MHz, CDCl$_3$): δ 6.81 (s, 1H), 6.59 (s, 1H), 6.27 (s, 2H), 6.01-6.03 (m, 2H), 5.48 (s, 1H), 4.77-4.78 (d, J=3.2 Hz, 1H), 4.62-4.63 (d, J=5.2 Hz, 1H), 4.29-4.31 (d, J=9.6 Hz, 2H), 3.77 (s, 6H), 3.14-3.19 (dd, J=5.2, 14.0 Hz, 1H), 2.91-2.97 (m, 1H).

ESI-MS (m/z): 448.1 [M+Na]$^+$ b. Synthesis of 4β-amino-4'-demethylepipodophyllotoxin (Compound 3)

At room temperature, 425 mg (1 mmol) of compound 2 and 100 mg of 10% Pd/C were suspended in dry methanol in a 100 mL round-bottom flask, and reduced by introducing hydrogen. The reaction was carried out overnight at room temperature. After the completion of the reaction was detected by TLC, the catalyst was removed by filtration, and the solution was evaporated to dryness under reduced pressure. The crude product was purified by silica gel column chromatography (dichloromethane:methanol=120:1) to give 320 mg of pure compound 3, which was a white solid. The yield was 80.2%.

$^1$H-NMR (400 MHz, CDCl$_3$): δ 6.81 (s, 1H), 6.50 (s, 1H), 6.31 (s, 2H), 5.95-5.98 (m, 2H), 4.56-4.57 (d, J=4.8 Hz, 1H), 4.29-4.31 (d, J=9.2 Hz, 2H), 4.21-4.22 (d, J=4.0 Hz, 1H), 3.78 (s, 6H), 3.27-3.32 (dd, J=5.2, 14.0 Hz, 1H), 2.82-2.85 (m, 1H).

$^{13}$C-NMR (100 MHz, CDCl$_3$): δ 175.41, 147.59, 147.27, 146.32, 134.11, 133.87, 131.23, 131.13, 110.23, 108.59, 107.92, 101.32, 68.14, 56.39, 48.89, 43.72, 40.22, 37.97.

ESI-MS (m/z): 400.1 [M+H]$^+$.

EXAMPLE 2

Synthesis of N,N,N'-trimethyl-N'-(4-carboxybenzyl)-1,3-propanediamine a. Synthesis of N,N,N'-trimethyl-N'-(4-tert-butoxycarbonylbenzyl)-1,3-propanediamine (Compound 6)

454 mg (2 mmol) of tert-butyl 4-chloromethylbenzoate (compound 4) was put into a 100 mL round-bottom flask, and 40 mL of anhydrous acetonitrile was added to dissolve it. Then 0.584 mL (4 mmol) of N,N,N'-trimethyl-1,3-propanediamine was dropped in. The reaction was carried out under stirring in 50° C. oil bath for 1 hour. After the completion of the reaction was detected by TLC, the solution was evaporated to dryness under reduced pressure. The crude product was purified by silica gel column chromatography (dichloromethane:methanol=25:1) to give 495 mg of pure compound 6, which was a faint yellow oil product. The yield was 80.9%.

$^1$H-NMR (400 MHz, CDCl$_3$): δ 7.92-7.94 (d, J=7.6 Hz, 2H), 7.35-7.37 (d, J=8.0 Hz, 2H), 3.52 (s, 2H), 2.37-2.41 (t, J=7.6 Hz, 2H), 2.28-2.32 (t, J=7.2 Hz, 2H), 2.23 (s, 6H), 2.18 (s, 3H), 1.67-1.71 (m, 2H), 1.59 (s, 9H).

ESI-MS (m/z): 307.2 [M+H]$^+$ b. Synthesis of N,N,N'-trimethyl-N'-(4-carboxybenzyl)-1,3-propanediamine (Compound 7)

Under condition of ice bath, 306 mg (1 mmol) of compound 6 was put into a 25 mL round-bottom flask, and 6 mL of dichloromethane was added to dissolve it. Then 2 mL of trifluoroacetic acid was slowly dropped in. The reaction was carried out under stirring for 3 hours in ice bath. After the completion of the reaction was detected by TLC, the solution was evaporated to dryness under reduced pressure to give a faint yellow oil product. The crude product was dissolved in a small amount of methanol, and hydrogen chloride was introduced therein. The product was salted under appropriate stirring, and the solution was evaporated to dryness under reduced pressure, followed by recrystallization in acetone-methanol to give 231 mg of pure compound 7, which was a white solid. The yield was 71.5%.

$^1$H-NMR (400 MHz, D$_2$O): δ 8.11-8.13 (d, J=7.6 Hz, 2H), 7.64-7.66 (d, J=8.0 Hz, 2H), 4.44-4.54 (d, J=37.6, 2H), 3.28 (s, 2H), 3.20-3.24 (t, J=8.0 Hz, 2H), 2.93 (s, 6H), 2.89 (s, 3H), 2.26 (s, 2H).

ESI-MS (m/z): 251.1 [M+H]$^+$.

EXAMPLE 3

Synthesis of Compound DC 200 mg (0.5 mmol) of compound 3 and 194 mg (0.6 mmol) of compound 7 were weighed and put in a 50 mL round-bottom flask, and 25 mL of anhydrous dichloromethane was added and stirred. Then 266 mg (0.7 mmol) of HATU and 251 μL (1.8 mmol) of triethylamine were added, stirred and reacted for 3 hours at room temperature. The solution was evaporated to dryness under reduced pressure. The crude product was purified by silica gel column chromatography (dichloromethane:methanol:triethylamine=20:1:0.2%) to give 260 mg of pure compound DC, which was a faint yellow solid. The yield was 82.4%.

$^1$H-NMR (400 MHz, CDCl$_3$): δ 7.71-7.73 (d, J=8.0 Hz, 2H), 7.39-7.41 (d, J=8.0 Hz, 2H), 6.82 (s, 1H), 6.32 (s, 2H), 6.55 (s, 1H), 5.97 and 5.99 (2s, 2H), 5.42-5.45 (m, 1H), 4.61-4.62 (d, J=4.8 Hz, 1H), 4.47-4.51 (m, 1H), 3.87-3.92 (m, 1H), 3.78 (s, 6H), 3.52 (s, 2H), 3.01-3.06 (m, 1H), 2.91-2.96 (dd, J=4.8, 14.0 Hz, 1H), 2.37-2.41 (t, J=7.2 Hz, 2H), 2.31-2.35 (t, J=7.6 Hz, 2H), 2.25 (s, 6H), 2.19 (s, 3H), 1.66-1.73 (m, 2H).

$^{13}$C-NMR (100 MHz, CDCl$_3$): δ 174.55, 167.37, 148.20, 147.47, 146.77, 143.87, 134.41, 132.72, 131.62, 129.75, 129.07, 128.91, 127.03, 109.97, 109.12, 107.67, 101.51, 69.20, 61.65, 57.57, 56.22, 55.36, 48.44, 45.29, 43.51, 42.13, 41.80, 37.37, 25.21.

ESI-MS (m/z): 632.3 [M+H]$^+$.

EXAMPLE 4

Synthesis of Compound DP 200 mg (0.5 mmol) of compound 3 and 184 mg (0.6 mmol) of compound 8 were weighed and put in a 50 mL round-bottom flask, 25 mL of anhydrous dichloromethane was added, and then 266 mg (0.7 mmol) of HATU and 251 μL (1.8 mmol) of triethylamine were added. The reaction was carried out under stirring at room temperature for 3 hours. The solution was evaporated to dryness under reduced pressure. The crude product was purified by silica gel column chromatography (dichloromethane:methanol:triethylamine=30:1:0.2%) to give 260 mg of pure compound DP, which was a faint yellow solid. The yield was 84.6%.

$^1$H-NMR (400 MHz, CDCl$_3$): δ 7.71-7.73 (d, J=8.0 Hz, 2H), 7.40-7.42 (d, J=8.0 Hz, 2H), 6.81 (s, 1H), 6.55 (s, 1H), 6.32 (s, 2H), 5.97 and 5.99 (2s, 2H), 5.41-5.44 (m, 1H), 4.60-4.61 (d, J=4.8 Hz, 1H), 4.47-4.51 (m, 1H), 3.86-3.91 (m, 1H), 3.78 (s, 6H), 3.55 (s, 2H), 3.03-3.06 (m, 1H), 2.91-2.95 (dd, J=5.2, 14.0 Hz, 1H), 2.48 (s, 8H) 2.30 (s, 3H).

¹³C-NMR (100 MHz, CDCl₃): δ 174.44, 167.30, 148.32, 147.56, 146.59, 142.89, 134.15, 132.71, 131.77, 130.06, 129.34, 128.80, 127.02, 110.04, 109.04, 107.74, 101.54, 69.18, 62.35, 56.29, 54.86, 52.89, 48.52, 45.83, 43.54, 41.82, 37.46.

ESI-MS (m/z): 616.3 [M+H]⁺.

EXAMPLE 5

Preparation of Injection Containing DC or DP 3.8 g of compound DC or DP was accurately weighed, 5% DMSO, 20% polyethylene glycol 400 and 20% absolute ethanol were added to help dissolution, and then water was added to make up the volume to 1000 mL. Pyrogen was adsorbed by activated carbon, successively filtered with a 0.45 μm and a 0.22 μm microporous filter membranes, and aseptically filled into a sterile ampoule to prepare an injection for intravenous injection.

EXAMPLE 6

In Vivo Distribution Experiment in Mice 16 mg of 4'-demethylepipodophyllotoxin was accurately weighed, 5% DMSO, 20% polyethylene glycol 400 and 20% absolute ethanol were added to help dissolution, so as to prepare an injection for intravenous injection with a concentration of 2 mg/mL. 28 mg of etoposide was accurately weighed, and 5% DMSO, 20% polyethylene glycol 400 and 20% absolute ethanol were added to help dissolution, so as to prepare an injection for intravenous injection with a concentration of 3.5 mg/mL. 30.40 mg of compound DC or DP was accurately weighed, and 5% DMSO, 20% polyethylene glycol 400 and 20% absolute ethanol were added to help dissolution, so as to prepare an injection for intravenous injection with a concentration of 3.8 mg/mL.

200 Kunming mice (male, 20±2 g) were used, which were fasted for 12 h before the experiment and given free access to water. In the experiment, they were randomly divided into 4 groups and administered by tail intravenous injection. The administration of 4'-demethylepipodophyllotoxin was carried out with a dosage of 10.00 mg/kg. Etoposide, compound DC and compound DP were administered in equimolar amount as 4'-demethylepipodophyllotoxin, and the administration dosages were etoposide 14.71 mg/kg, compound DC 15.78 mg/kg, and compound DP 15.38 mg/kg, respectively. 5 minutes, 15 minutes, 30 minutes, 1 hour, 2 hours, 4 hours, 8 hours, 12 hours, 24 hours and 48 hours after administration, the blood was collected and the mice sacrificed in all groups. The whole blood was put into sodium heparin-containing EP tubes, centrifuged at 5000 rpm at 4° C. for 5 min, and the upper plasma was collected and frozen at −40° C. for use. The hearts, livers, spleens, lungs, kidneys, brains and pancreas of the mice were immediately separated, and the residual blood was washed away with physiological saline. The remaining water on the surfaces of the organs was absorbed with filter papers. The organs were weighed and physiological saline 2 times the volume of the organs was added for homogenization.

0.1 mL of mouse plasma and 0.1 mL of tissue homogenate were taken and put into a 0.5 mL EP tube, 0.3 mL of methanol was added to all the samples as a protein precipitant. The sample was subjected to vortex vibration for 5 minutes, and then centrifuged at 13000 rpm at 4° C. for 10 min. The supernatant was taken and filtered with a 0.22 μm organic filtration membrane, and 1 μL of the sample was taken and subjected to LC-MS/MS analysis.

LC-MS/MS Analysis Condition

Liquid phase conditions: Agilent 1200 Series High Resolution Rapid LC System (RRLC); chromatographic column: Agilent Diamonsil ODS column (50 mm×4.6 mm, 1.8 μm); mobile phase: for 4'-demethylepipodophyllotoxin, methanol:0.1% formic acid aqueous solution=50:50, for etoposide, acetonitrile:0.1% formic acid aqueous solution=35:65, for compound DC, methanol:0.1% formic acid aqueous solution=45:65, and for compound DP, methanol:0.1% formic acid aqueous solution=34:66; flow rate: 0.4 mL/min; column temperature: 30° C.; and injection volume: 1 μL.

Mass spectra conditions: Agilent Triple Quadrupole Mass Spectrometry (6410B); the analytes were subjected to a multiple reaction monitoring (MRM) in positive mode: for 4'-demethylepipodophyllotoxin, etoposide, compound DC and compound DP, fragmentation voltages were 97 V, 148 V, 190 V and 169 V, respectively; collision cell voltages were 20 V, 12 V, 52 V and 36 V, respectively; and ionic reactions (m/z) were 401.1→185, 589.2→229, 632.3→86.1 and 616.3→58.1, respectively; drying gas temperature: 350° C.; drying gas flow rate: 10 L/min; atomization air pressure: 30 psi; and the capillary voltage: 4000V.

Each pharmacokinetic parameters were calculated by DAS3.2.5 software, and the formula for calculating the targeting ability evaluation index, i.e., peak concentration ratio Ce and relative uptake rate Re, were shown hereinafter.

$$Ce_{lung} = (C_{max,lung})_{compound} / (C_{max,lung})_{drug\ or\ control}$$

$$Re_{lung} = (AUC_{0-t,lung})_{compound} / (AUC_{0-t,lung})_{drug\ or\ control}$$

or a pharmaceutically acceptable salt thereof.

Results of FIG. 1 showed that 5 minutes after administration by tail intravenous injection, the concentrations of compound DC and DP in the lung were much higher than 4'-demethylepipodophyllotoxin original drug group and etoposide control group. Based on the peak concentration ratio Ce, the peak concentration of compound DC in the lung was 5.29 times and 4.54 times of that of 4'-demethylepipodophyllotoxin original drug group and etoposide control group, respectively; and the peak concentration of compound DP in the lung was 5.41 times and 4.65 times of that of 4'-demethylepipodophyllotoxin original drug group and the etoposide control group, respectively.

Figure 2:
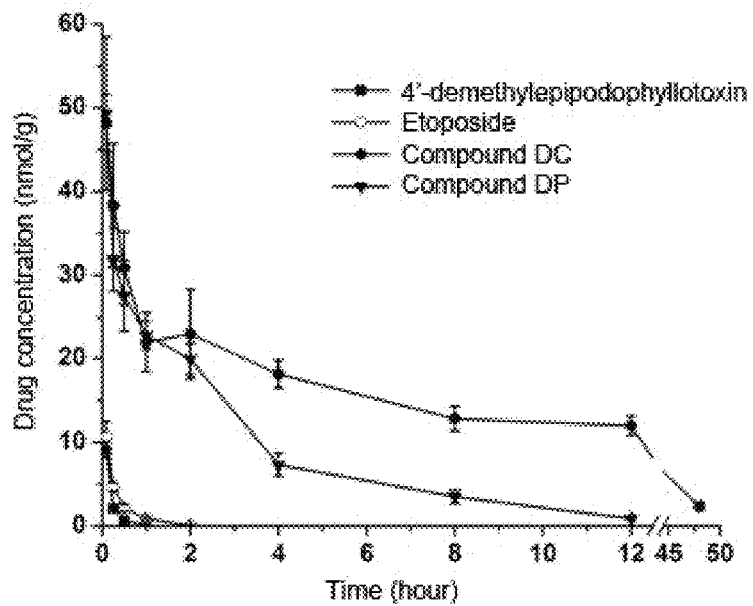
FIG. 2 is a concentration-time curve of 4'-demethylepipodophyllotoxin, etoposide, compound DC and compound DP in lung after administration by tail vein injection.

The results in FIG. 2 showed that after administration of compound DC and DP by tail intravenous injection, the drug concentrations in the lung were much higher than that of 4'-demethylepipodophyllotoxin original drug group and etoposide control group at each time point. One hour after the administration, the concentration of 4'-demethylepipodophyllotoxin (original drug) in the lung was below the detectable limit. Two hours after the administration, the concentration of etoposide (control) in the lung was below the detectable limit. However, compounds DC and DP still maintained at a relatively high drug concentration and lasted for up to 48 hours and 12 hours, respectively, significantly prolonging the retention time of the drug in the lung. Based on the relative uptake rate Re, the lung relative uptake rate of compound DC was 168.38 times and 98.16 times of that of 4'-demethylepipodophyllotoxin original drug group and etoposide control group, respectively; and the lung relative uptake rate of compound DP was 42.56 times and 24.81 times of 4'-demethylepipodophyllotoxin original drug group and etoposide control group, respectively.

The above experiment results show that compound DC and DP have obvious lung-targeting ability, which significantly improves the accumulating concentration of drug in lung, and prolongs the retention time in lung, so as to decrease the administration dosage of the drug and decrease the toxicity and side effects.

EXAMPLE 7

In Vivo Curative Efficacy Test in Mice

The experiment was performed according to the method reported by Small, 2014(3):524-535. C57BL/6 mice (male, 20±2 g, 6 to 8 week-old) were used and intravenously injected with mouse melanoma B16 cells in logarithmic growth phase. $5 \times 10^5$ cells were injected into each mouse to establish a melanoma lung metastasis model, and the mice were randomly divided into 5 groups (recorded as the 0th day). The injections for intravenous injecting used in the experiment were prepared according to Example 6. On the 4th, 7th and 13th day after the modeling, each group was subjected to intravenous injection for four times. 4'-demethylepipodophyllotoxin was provided at a dosage of 5.00 mg/kg, and etoposide, compound DC and compound DP were provided at equimolar amount with 4'-demethylepipodophyllotoxin, and the administration dosages were etoposide 7.36 mg/kg, compound DC 7.89 mg/kg, and compound DP 7.69 mg/kg, respectively. The control group was administered with equal amount of solvent. All mice were housed normally and sacrificed on the $22^{nd}$ day after modeling. The lung tissue was immediately separated out, washed with physiological saline and weighed, and the number of tumor nodules was calculated.

Figure 3:
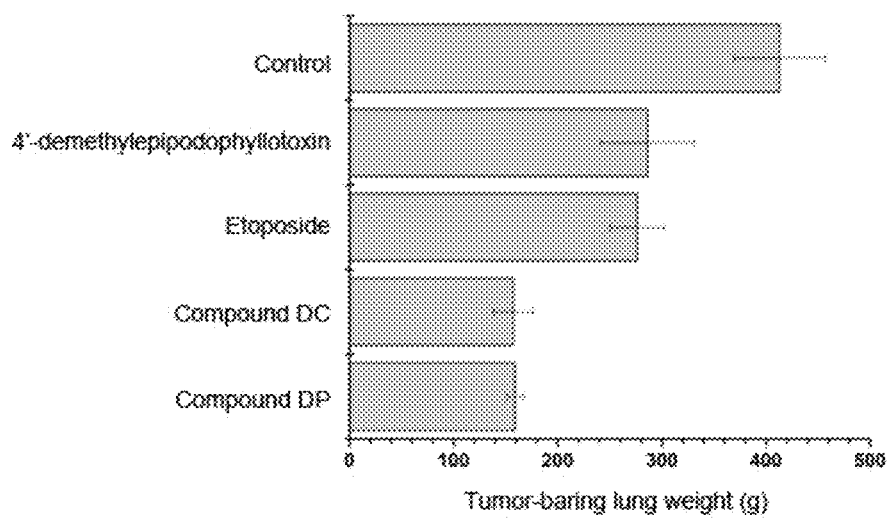
FIG. 3 shows the tumor-bearing lung weight after melanoma lung metastasis tumor is treated with 4'-demethylepipodophyllotoxin, etoposide, compound DC and compound DP.
Figure 4:
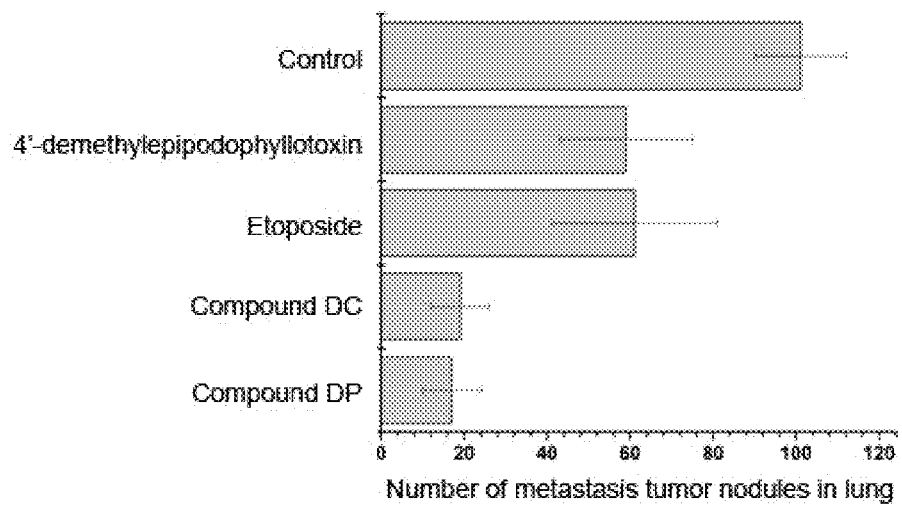
FIG. 4 shows the number of metastasis tumor nodules after melanoma lung metastasis tumor is treated with 4'-demethylepipodophyllotoxin, etoposide, compound DC and compound DP.

The results of the FIG. 3 and FIG. 4 showed that after establishing a mouse melanoma lung metastasis model, severe lung metastasis tumor appeared in the control group, demonstrating that the model was established successfully in the experiment. The other administration groups have different degrees of inhibitory effects on lung metastatic tumor. Comparing with the control group, 4'-demethylepipodophyllotoxin group and etoposide group have improved the lung metastatic tumor to a certain degree, reduced the tumor-bearing lung weight, and decreases the number of lung metastasis tumor nodules. Compound DC group and DP group have the best curative effects, which were significantly better than that of 4'-demethylepipodophyllotoxin group and etoposide group, with the least tumor-bearing lung weight and the number of lung metastasis tumor nodules.

The above experiment results demonstrate that compounds DC and DP have significant lung-targeting effect, and they have stronger inhibition effect and better drug effect for lung tumor.

The invention claimed is:

1. A compound of the following structure

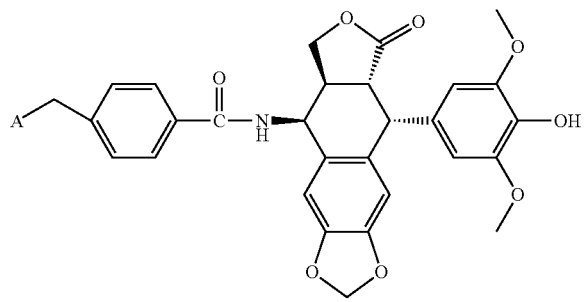

or a pharmaceutically acceptable salt thereof;
wherein:
A is

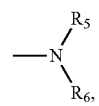

, and $R_5$ is C1-C3 alkyl, $R_6$ is di-(C1-C3 alkyl)amino C1-C3alkyl,
or A is selected from the group consisting of

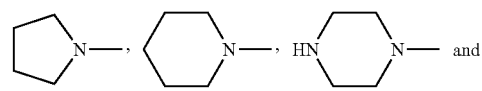

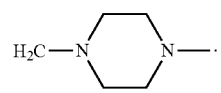

2. The compound according to claim 1, which is:

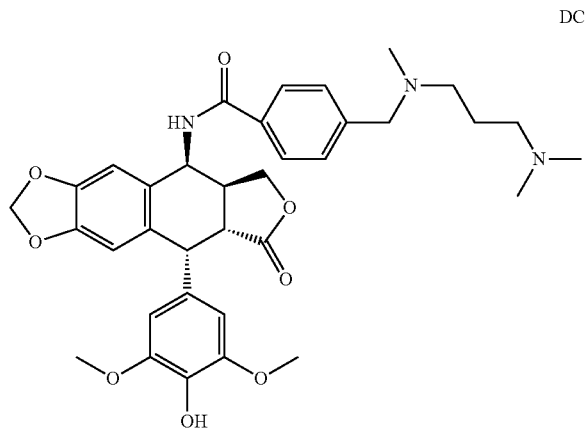 [SMILES: COc1cc([C@@H]2c3cc4c(cc3[C@@H](NC(=O)c3ccc(CN(C)CCCN(C)C)cc3)[C@H]3COC(=O)[C@H]23)OCO4)cc(OC)c1O]

or a pharmaceutically acceptable salt thereof.

3. The compound according to claim 1, which is:

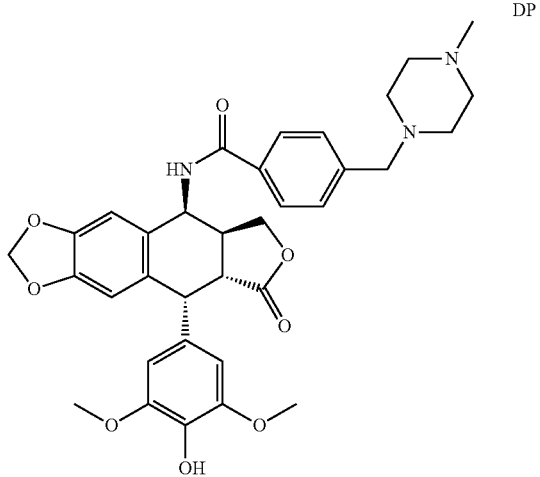 [SMILES: COc1cc([C@@H]2c3cc4c(cc3[C@@H](NC(=O)c3ccc(CN5CCN(C)CC5)cc3)[C@H]3COC(=O)[C@H]23)OCO4)cc(OC)c1O]

or a pharmaceutically acceptable salt thereof.

4. The compound or the pharmaceutically acceptable salt thereof according to claim 1, wherein the pharmaceutically acceptable salt thereof is a salt formed from the compound and an inorganic acid or an organic acid, comprising hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, niacin, camphoric acid, gluconic acid, glucuronic acid, pamoic acid, methanesulfonic acid, ethanesulfonic acid, sulfamic acid and p-toluenesulfonic acid.

5. A pharmaceutically acceptable preparation, comprising the compound or the pharmaceutically acceptable salt thereof according to claim 1, wherein the preparation is selected from tablet, suppository, soft capsule or hard capsule, solution, suspension or aerosol, injection, lyophilized powders for injection, sustained-release controlled-release preparation and particle drug delivery system, and wherein the preparation is administered by a manner of mouth, nasal, rectal, transdermal or injection.

6. The preparation according to claim 5, which is an injection.

* * * * *